United States Patent [19]

Dancer et al.

[11] Patent Number: 5,786,165
[45] Date of Patent: Jul. 28, 1998

[54] HERBICIDE TEST METHOD

[75] Inventors: Jane Elizabeth Dancer, Saffron Walden, England; Stephen David Lindell, Frankfurt am Main, Germany

[73] Assignee: Agrevo UK Limited, Cambridge, England

[21] Appl. No.: 765,880

[22] PCT Filed: Jun. 22, 1995

[86] PCT No.: PCT/EP95/02423

§ 371 Date: Jan. 2, 1997

§ 102(e) Date: Jan. 2, 1997

[87] PCT Pub. No.: WO96/01326

PCT Pub. Date: Jan. 18, 1996

[30] Foreign Application Priority Data

Jul. 2, 1994 [GB] United Kingdom ............ 9413343

[51] Int. Cl.⁶ ............ C12Q 1/34; C12Q 1/37; C12Q 1/00; C12N 15/00
[52] U.S. Cl. ............ 435/18; 435/23; 435/24; 435/4; 435/69.2; 435/68.1; 536/22.1; 536/27.6; 536/26.26; 504/116; 935/64; 935/67; 800/200
[58] Field of Search ............ 435/18, 23, 24, 435/4, 69.2, 68.1; 504/116; 935/64, 67; 536/22.1, 27.6, 26.7, 26.26; 800/200

[56] References Cited

U.S. PATENT DOCUMENTS

| 5,180,873 | 1/1993 | Jorgensen | 800/205 |
| 5,254,801 | 10/1993 | Dotson et al. | 800/205 |
| 5,304,481 | 4/1994 | Davies et al. | 435/18 |
| 5,424,412 | 6/1995 | Brown et al. | 800/205 |
| 5,558,862 | 9/1996 | Corbin et al. | 800/205 |

FOREIGN PATENT DOCUMENTS 9601326  1/1996  WIPO.

OTHER PUBLICATIONS

Dancer et al; "Bioorg. Med. Chem. Lett.", vol. 6(17), pp. 2131–2136, 1996. Month Not Available.

*Primary Examiner*—Louise N. Leary
*Attorney, Agent, or Firm*—Ostrolenk, Faber, Gerb & Soffen, LLP

[57] ABSTRACT

Potential herbicides can be identified by testing compounds in an AMP deaminase inhibition assay. Also disclosed is the use as a herbicide of a compound which is an inhibitor of AMP deaminase in planta and causes elevated ATP levels in susceptible plants.

8 Claims, No Drawings

HERBICIDE TEST METHOD

FIELD OF THE INVENTION

This invention relates to a method for identifying potential herbicides and the use of inhibitors, or pro-inhibitors, of AMP deaminase as herbicides.

PRIOR ART

Coformycin and carbocyclic coformycin have previously been reported to have herbicidal activity (Isaac et al (1991), J. Antibiotics 44, 729 and Bush et al (1993), Phytochem. 32, 737 respectively).

Coformycin is known to be a potent inhibitor of the enzyme adenosine deaminase, EC 3.5.4.4 (Nakamura et al 1974, J. Am. Chem. Soc. 96, 4327). Coformycin is also an inhibitor of the related enzyme AMP deaminase, EC 3.5.4.6, although phosphorylation at position 5' of the ribose is required to achieve very potent inhibition (Frieden et al, 1980, Biochem. 19, 5303; Merkler et al, 1990, Biochem., 29, 8358).

Inhibitors of adenosine deaminase are of interest for cancer chemotherapy, as immunosuppressive agents for autoimmune disease, and for their ability to enhance the activity of adenine nucleoside analogues for the treatment of viral diseases and cancer that could be rendered inactive through the action of the enzyme [Gilbertson and Sircar (1990) in Comprehensive Medicinal Chemistry (Eds Hansch C., Sammes P. G. and Taylor J. B., Vol 2, pp 449)]

It is generally accepted that plants do not contain adenosine deaminase [Holloman (1979), Proc. Brit. Crop Conf. Pests Diseases, 251; Batlers et al (1985), Physiol. Plant Pathol., 27, 65; Brady and Hegarty (1966), Nature, 209, 1027; Staub et al (1985), J. Am. Soc. Hort. Sci., 110, 426; Le Floch et al (1982), Plant Sci. Lett., 27, 309]. Consequently, the herbicidal activity of coformycin cannot be due to its known ability to inhibit this enzyme. While the related enzyme AMP deaminase has been proposed to have a role in maintaining the intracellular adenylate energy charge in plants (Raymond et al, 1987, in The Biochemistry of Plants, Vol II, Chapter 5, pp 129, Ed: Davis D. D.), no direct experimental evidence has been published, to our knowledge, to support this theory in plants. Although coformycin has been reported to perturb adenine nucleotide levels in a suspension culture of *Catharanthus roseus*, inhibition of AMP deaminase was not directly demonstrated (Yabuki and Ashihara, 1991, Biochim. Biophys. Acta, 1073, 474) and coformycin is known to be a relatively weak inhibitor of this enzyme when compared both to its effects on adenosine deaminase and the potency of its 5'-phosphate derivative against AMP deaminase.

We have discovered that the potent herbicidal activity of carbocyclic coformycin is due to phosphorylation of the compound in planta and subsequent inhibition of the enzyme AMP deaminase (EC 3.5.4.6). This mode of action has not previously been described for herbicides.

DISCLOSURE OF THE INVENTION

We have shown carbocyclic coformycin to be a potent inhibitor of mammalian adenosine deaminase (Test Example 1).

Investigations of the metabolism of $^{14}$C-adenosine by crude, desalted homogenates from pea seedlings confirmed the literature data that adenosine deaminase was not present. The related enzyme, AMP deaminase was, however, clearly present (Test Example 2).

Application of carbocyclic coformycin to pea seedlings via the transpiration stream resulted in a rapid decrease in the extractable levels of AMP deaminase (Test Example 3).

Although carbocyclic coformycin was only a relatively poor inhibitor of plant AMP deaminase, its 5'-phosphate derivative was a potent inhibitor (Test Example 4).

The above observations suggested that carbocyclic coformycin was phosphorylated in planta and that this phosphorylated derivative caused the observed reduction in the levels of the enzyme activity. Further evidence that phosphorylation does occur in vivo was provided by the application of $^3$H-carbocyclic coformycin to pea seedlings via the transpiration stream and monitoring the metabolites formed. A compound that co-chromatographed with authentic carbocyclic coformycin-5'-phosphate was shown to be formed and, moreover, this compound could be isolated bound to a soluble protein fraction containing AMP deaminase, providing strong evidence that the 5'-phosphate derivative does inhibit the enzyme in planta (Test Example 5).

AMP deaminase has been proposed to have a role in maintaining the intracellular adenylate energy charge [Raymond et al (1987), in The Biochemistry of Plants, Vol 11 (Ed Davis D D), Chapter 5, pp 129].

We have clearly demonstrated the importance of this enzyme to the well being of a plant in view of the potent herbicidal effects obtained when the enzyme is inhibited. Its role in maintaining the adenylate energy change was also evident from analysis of the effects of the application of carbocyclic coformycin on adenylate levels. As shown in Test Example 6, a remarkable rise in extractable levels of ATP was evident. This rise in ATP levels appears to be unique to inhibitors of AMP deaminase and was not shown, for example, by the standard herbicide chlorsulfuron.

These results establish AMP deaminase inhibition as the mode of action for carbocyclic coformycin. This is a novel herbicidal mode of action and its discovery opens up the opportunity of identifying novel chemicals that inhibit the same enzyme target either directly or following metabolism to an active inhibitor in planta ("indirect inhibitors").

Thus the invention also provides a method for identifying potential herbicides which comprises testing a candidate in either an AMP deaminase inhibition assay for direct inhibitors or an adenosine deaminase assay for inhibitors that require conversion in planta.

The invention still further provides the use as a herbicide of a compound which is an AMP deaminase inhibitor in planta, with the proviso that the compound is not a general enzyme inhibitor and is not a compound previously known to have herbicidal activity.

In this use, the AMP deaminase inhibitor is one which produces a measurable reduction in AMP deaminase when tested against an enzyme preparation at 100 μM or less. By "measurable reduction" is generally meant at least 25% reduction and preferably at least 50% reduction of this rate.

In this use, an indirect inhibitor is one which is converted in planta to an inhibitor of AMP deaminase. Some indirect inhibitors will produce a measurable reduction in adenosine deaminase when tested against an enzyme preparation at 100 μM or less. By "measurable reduction" is generally meant at least 25% reduction and preferably at least 50% reduction at this rate.

Although the AMP deaminase assays will identify the intrinsic herbicidal activity, it is subsequently necessary to use conventional tests to confirm the in vivo herbicidal activity. This, of course, is essential for all indirect inhibitors that require activation through metabolism in planta. Typical symptoms resulting from treatment with carbocyclic coformycin are cessation of growth followed by paling and necrosis at the apical meristem. As these symptoms are similar to those caused by other herbicides with an unrelated mode of action (eg chlorsulfuron), confirmation that a candidate compound does exert its herbicidal activity through inhibition of AMP deaminase can be obtained through measurement of the extractable ATP levels. To the best of our belief, an increase in ATP levels is uniquely associated with herbicides that exert their mode of action through inhibition of AMP deaminase. In this case, the active compound is one which produces a measurable increase in extractable ATP levels when applied to plants via the transpiration stream at 10 mM or less. By "measurable increase" is generally meant at least an increase to 1.5 fold of the control value and preferably an increase to at least 2.0 fold of the control value.

Test Example 1
Mammalian Adenosine Deaminase Inhibition Assay

A suitable source of enzyme is calf intestinal mucosa adenosine deaminase supplied by the Sigma Chemical Company Limited. The assay employed follows the protocol provided by the supplier and measures a decrease in absorption at 265 nm as the substrate adenosine is utilized. A 10 minute preincubation of enzyme and inhibitor prior to addition of the substrate was employed. Under these conditions, carbocyclic coformycin gave 50% inhibition at 25 nM when the substrate concentration was 60 µM.

Test Example 2
Adenylate Metabolism Pathway in a Crude Plant Homogenate

Peas (*Pisum sativum L var* Onward) were grown in soil for 10 days at 25° C. with a 16 hour/8 hour light/dark cycle. The seedlings were harvested close to soil level and a crude homogenate of was prepared by homogenization in 2 volumes of ice cold buffer containing tris-HCl (0.1M, pH 7.4 with 5M NaOH), 0.1 mM dithiothreitol and 0.4M sucrose using a Waring blender (1 minute, top speed). The homogenate was passed through 6 layers of muslin and 2.5 ml desalted on a sephadex (Registered Trade Mark) PD10 column (1.5 cm×8 cm) which had been pre-equilibrated with the homogenization buffer. Protein was eluted using the same buffer. The assay contained, in a total volume of 250 µl, 50 mM Tris-HCl (pH 6.5), 50 mM KCl, 0.05% (w/v) BSA and 100 mg protein. ATP (5 mM) was also included where indicated. The assay was started by the addition of [$^{14}$C] adenosine (500 µM, 0.2 µCi). After incubation at 25° C. for 10 minutes, the reaction was stopped by the addition of 0.25 ml ice cold HClO$_4$ (0.4M). Precipitated protein was removed by centrifugation (13,000 g, 2 minutes) and 0.4 ml of the resulting supernatant applied to phenylsilane bonded silica gel columns (500 mg) which had been previously washed with 2 volumes of methanol and then 2 ml 0.4M HClO$_4$. Samples were eluted with 4 ml 0.4M HClO$_4$. The pH of the eluate was adjusted on ice to between 5.5 and 7.0 with 5M KOH. The neutralised extract was centrifuged (13,000 g, 2 minutes) and evaporated to dryness in a Gyrovap (Registered Trade Mark). The sample was then re-dissolved in 0.5 ml 10 mM HCl and centrifuged (13,000 g, 2 minutes) prior to HPLC analysis. The products were analysed using reverse phase chromatography with a spherisorb (Registered Trade Mark) column (25 cm×0.46 cm), solvent 1: 95:5 10 mM KH$_2$PO$_4$: methanol; solvent 2: 88:12 10 mM KH$_2$PO$_4$: methanol, pH 5.3, step change at 6 minutes, Flow rate: 1 ml/minute.

The data outlined in the table below, clearly indicate that no adenosine deaminase activity was detectable. Indeed, no metabolism of adenosine was noted at all unless ATP was also added. Addition of ATP led to the formation of the phosphorylated compounds AMP, ADP and ATP, as would be expected from the action of the appropriate kinases. The formation of IMP is presumably due to the action of AMP deaminase and the small amount of inosine due to subsequent dephosphorylation.

| | % of radiolabel as: | | | | | |
|---|---|---|---|---|---|---|
| | adenosine | inosine | AMP | IMP | ADP | ATP |
| [$^{14}$C] adenosine | 100 | 0 | 0 | 0 | 0 | 0 |
| [$^{14}$C] adenosine + 5 mM ATP | 40 | 2 | 20 | 15 | 15 | 8 |

Test Example 3
Effects of Carbocyclic Coformycin on Extractable Levels of AMP Deaminase Pea seedlings were excised near soil level, the stems quickly washed with distilled water and then stood upright in a 1 ml cuvette containing 2 ml of compound solution or water (control). A section (approx 2 mm) was cut from the base of the stem while it was immersed to prevent air locks from forming in the xylem. The seedlings were incubated in the light at room temperature (approx 20° C.) in a moving air stream. At intervals, individual seedlings were extracted and the levels of AMP deaminase determined by extraction in 2 volumes ice cold citrate buffer (0.1M, pH 7), 0.5 mM dithiothreitol using a pestle and mortar. The homogenate was passed through 6 layers of muslin and loaded onto a sephadex gel filtration column (1.5 cm×8 cm) which had previously been equilibrated with 30 mM citrate (pH 7.1), 50 mM KCl and 0.5% (w/v) BSA (Assay buffer). The protein was eluted using the assay buffer and used directly for the enzyme assay. The assay is based on the release of ammonia (McCullough (1967), Clinica Chimica Acta, 17, 297) and contained in a total volume of 0.5 ml 60 mM citrate buffer (pH 7.1 with 5M NaOH) 100 mM KCl, 0.1% (w/v) BSA and 5 mM AMP. The reaction was started by the addition of 50 µl extract. At 15 minute intervals from 0 to 60 minutes, the reaction was stopped by the addition of 420 µl reagent 1 (0.1M phenol, 0.17 mM sodium nitroprusside) immediately followed by 275 µl reagent 2 (0.125M NaOH, 0.38M Na$_2$HPO$_4$ and 5 ml HOCl in a total volume of 500 ml). Following incubation for 60 minutes at 55° C., the absorbance of the solutions at 625 nm was determined.

Under these conditions and treatment for 1 hour, the extractable levels of AMP deaminase were reduced to 20–30% of the control levels of 19 µmols ammonia release per gram fresh weight per minute.

Test Example 4
Plant AMP Deaminase Inhibition Assay

Pea seedlings were grown as described in Test Example 2. The seedlings were harvested close to soil level and homogenized in 2 volumes of ice cold phosphate buffer (pH 7.5) containing 0.1 mM dithiothreitol and 0.4M sucrose using a Waring blender (1 minute, top speed). All of the following operations were carried out at 4° C. The homogenate was filtered through 6 layers of muslin and centrifuged at 100,000 g for 20 minutes to remove cell debris. To the resulting supernatant was added 40% (w/v) ammonium sulphate while stirring constantly. The precipitate was collected by centrifugation (12,000 g, 15 minutes) and dissolved in 30 ml phosphate buffer (pH 7.5), 0.1 mM dithiothreitol then dialyzed overnight against 2 l of the same buffer. Insolubles formed during the overnight dialysis were removed by centrifugation (7,000 g, 10 minutes). The supernatant was applied to a phospho-cellulose column (1.5×8 cm) which had been pre-equilibrated with 0.1M phosphate buffer (pH 7.5). After loading, the column was washed with 14 ml phosphate buffer (0.1M, pH 7.5) and the enzyme eluted with 0.6M phosphate buffer (pH 7.5). Activity was determined using the ammonia release assay described in Test Example 3 above.

Using a 10 minute preincubation period and a substrate concentration of 640 µM, carbocyclic coformycin gave 50% inhibition of the activity at 120 µM. In contrast, carbocyclic coformycin 5'-phosphate gave 50% inhibition at 20 nM.

Test Example 5
In Planta Metabolism of carbocyclic Coformycin

Pea seedlings were grown as described in Test Example 2, harvested as described in Test Example 3 and then supplied with 10 µM (400 Ci mol$^{-1}$) [$^3$H] carbocyclic coformycin via the transpiration stream. After incubation periods, pairs of seedlings were rapidly frozen in liquid nitrogen, ground to a fine powder and extracted in 2 ml ice cold 0.4M HClO$_4$. The extracts were processed for HPLC analysis as described in Test Example 2 above except that the final sample was resuspended in 0.5 ml water instead of 10 mM HCl. [$^3$H] carbocyclic coformycin and [$^3$H] carbocyclic coformycin 5'-phosphate were separated using cation exchange chromatography with a Partisil (Registered Trade Mark) SCX column (8.0 cm×0.46 cm), 0.05M NH$_4$H$_2$PO$_4$, pH 2.6; flow rate=2 ml/minute.

After 4 hours incubation, the major metabolite co-chromatographed with authentic carbocyclic coformycin 5'-phosphate. Additional proof for the identity of the metabolite was evident from the fact that alkaline phosphatase treatment resulted in complete reconversion of the metabolite to carbocyclic coformycin.

When plants treated as above were extracted according to the enzyme extraction protocols given in Test Example 3, radioactivity was also associated with the protein fraction containing AMP deaminase. Denaturation of the protein and subsequent HPLC analysis showed all the radioactivity to be associated with carbocyclic coformycin 5'-phosphate.

Test Example 6
Measurement of Extractable ATP Levels

Peas were grown as described in Test Example 1 and exposed to carbocyclic coformycin via the transpiration stream as outlined in Test Example 3. Individual seedlings were rapidly frozen in liquid nitrogen. The frozen tissue was ground to a fine powder using a pestle and mortar then 1 ml ice cold 0.4M HClO$_4$ was added. The frozen acid was ground to a fine powder tissue, the mixture allowed to thaw and then incubated on ice for 15 minutes. The extract was centrifuged (4,000 rpm, 5 minutes).

ATP measurements were made using the luciferase assay and a LUMAC Biocounter M2500 (6370 AC Landgraaf, The Netherlands). Samples were diluted 1:10,000 in water and 100 µl was assayed according to the manufacturer's instructions.

After 4 hours treatment, 100 µM carbocyclic coformycin increased the ATP levels to approximately twice the control levels of 333 nmols ATP per gram fresh weight.

We claim:

1. A method for identifying potential herbicides which comprises testing a compound in an AMP deaminase inhibition assay and where a measurable reduction of AMP deaminase is observed the compound is subsequently subjected to conventional test(s) to confirm the in vivo herbicidal activity, said measurable reduction comprising at least 25% reduction of AMP deaminase when tested against an enzyme preparation at 100 µM or less.

2. A method for identifying potential herbicides that could be metabolized to an inhibitor of AMP deaminase in planta which comprises testing a compound in an adenosine deaminase inhibition assay and where a measurable reduction of adenosine deaminase is observed the compound is subsequently subjected to conventional test(s) to confirm the in vivo herbicidal activity, said measurable reduction comprising at least a 25% reduction of adenosine deaminase when tested against an enzyme preparation at 100 µM or less.

3. Herbicides identified by the method claimed in claim 1.

4. A method of combating weeds comprising treatment with a herbicide of a compound which is an inhibitor of AMP deaminase in planta and causes elevated ATP levels in susceptible plants, with the proviso that the compound is not a general enzyme inhibitor and is not a compound previously known to have herbicidal activity.

5. The method according to claim 4 wherein the compound is one which produces either at least a 25% reduction in AMP deaminase activity when tested against a plant enzyme preparation at 100 µM and/or causes a measurable increase in extractable ATP levels when applied by transpiration feeding at 10 mM, said measurable increase being at least 1.5 of the control value in extractable ATP levels when applied to plants via the transpiration stream at 10 mM or less.

6. Herbicides identified by the method claimed in claim 2.

7. The method for identifying potential herbicides according to claim 2 in which said measurable reduction is at least 50%.

8. The method for identifying potential herbicides according to claim 1 in which said measurable reduction is at least 50%.

* * * * *